United States Patent [19]

Sakamaki et al.

[11] Patent Number: 4,952,566

[45] Date of Patent: Aug. 28, 1990

[54] STABILIZED ANTHRACYCLINE PREPARATION CONTAINING L-CYSTEINE

[75] Inventors: Yasuhisa Sakamaki, Hyogo; Yukio Ozaki; Norihiko Tanno, both of Osaka, all of Japan

[73] Assignee: Sumitomo Pharmaceuticals Co., Ltd., Osaka, Japan

[21] Appl. No.: 227,135

[22] Filed: Aug. 2, 1988

[30] Foreign Application Priority Data

Aug. 5, 1987 [JP] Japan ................................. 62-197032

[51] Int. Cl.$^5$ .............................................. A61K 31/70
[52] U.S. Cl. ....................................... 514/34; 514/788; 536/6.4
[58] Field of Search .................................. 514/34, 788

[56] References Cited

U.S. PATENT DOCUMENTS

| | | | |
|---|---|---|---|
| 4,673,668 | 6/1987 | Ishizumi et al. | 514/34 |
| 4,675,311 | 6/1987 | Gatti et al. | 514/34 |

FOREIGN PATENT DOCUMENTS

| | | | |
|---|---|---|---|
| 0072259 | 2/1983 | European Pat. Off. | 514/34 |
| 0107486 | 5/1984 | European Pat. Off. | 514/34 |
| 2165751 | 4/1986 | United Kingdom | 514/34 |

OTHER PUBLICATIONS

Serial No. 6,190,064, 9/1980, Meyers et al.
Serial No. 6,100,496, 12/1979, Myers et al.
Serial No. 6,024,246, 3/1979, Myers et al.
Formula Chart of Compound A.
Merck Indices for Daunorubicin.
Merck Index reference to Doxorubicin.
Recent technique in preparation and application thereof, III,IV, 1, pp. 135–138, 1986.

*Primary Examiner*—Johnnie R. Brown
*Assistant Examiner*—Elli Peselev
*Attorney, Agent, or Firm*—Cushman, Darby & Cushman

[57] ABSTRACT

A stabilized preparation, particularly, freeze-drying injection, of anthracycline, for example, (7S, 9S)-9-acetyl-9-amino-7-[(2-deoxy-β-D-erythropentopyranosyl-)oxy]-7,8,9,10-tetrahydro-6,11-dihydroxynaphthacene-5,12-dione or salts thereof which comprises L-cysteine or salts thereof.

7 Claims, No Drawings

STABILIZED ANTHRACYCLINE PREPARATION CONTAINING L-CYSTEINE

The present invention relates to an anthracycline preparation, more particularly to a preparation of (7S, 9S)-9-acetyl-9-amino-7-[(2-deoxy-$\beta$-D-erythro-pentopyranosyl)oxy]-7,8,9,10-tetrahydro-6,11-dihydroxynaphthacene-5,12-dione (hereinafter referred to as compound A) or salts thereof stabilized with L-cysteine or salts thereof.

Anthracyclines including the compound A or salts thereof (Japanese patent Kokai Sho 58-194846) are unstable in solution. Liquefying injection before using, e.g., powder filling or a freeze-drying product, is familiar to the skilled when such a pharmaceutical preparation as injection is prepared from such compounds ("Recent technique in preparation and application thereof" III, IV. 1, p. 135, 1986, published by Iyaku Journal Co., Ltd.).

Sufficient stabilization of the compound A or salts thereof is hardly expected even after freeze-drying. Storage at room temperature for a long period of time or ill-treat storage causes degradation in potency, formation of hardly soluble deposition substances and/or turbidity in re-dissolution. It is beyond expectation to have found that addition of L-cysteine or salts thereof overcomes such difficulties as mentioned above.

The present invention provides a stabilized freeze-drying preparation of anthracycline by having L-cysteine or salts thereof added thereto. Hereinafter, explanation is made referring to the compound A or salts thereof.

thereof in distillated water for injection, adding a small amount each of sodium hydroxide and hydrochloric acid in order to adjust pH, making sterile filtration, filling the sterile filtrate in vials and subjecting to freeze-drying to prepare powdery preparation for injection. Injection is stored as it is and water is added thereto just before it is applied to.

Acids which are utilized for salts of anthracycline including the compound A are, for example, hydrochloric acid, hydrobromic acid, citric acid, tartaric acid, lactic acid, fumaric acid, maleic acid, and methanesulfonic acid.

Salts of L-cysteine are usually in the hydrochloride form. Alternatively, they may be sulfate.

The following examples will be helpful to understand the nature of the present invention.

EXAMPLE 1

To hydrochloride of the compound A (20 mg potency) containing lactose, a filler, (50 mg), were added L-cysteine hydrochloride, citric acid, sodium dihydrogenphosphate, maleic acid or glycine hydrochloride, respectively, until pH was adjusted to 2.5–3.5. The mixtures were dissolved in distillated water for injection and then a small amount each of sodium hydroxide and hydrochloric acid was added thereto until pH was adjusted to about 3.

The solution was filtered under sterilization and was filled in vials (18 ml each) and subjected to freeze-drying. Stability of the products stored at 60° C. for 3 days and 7 days was shown in Table 1 together with that of a product prepared in the same procedure as above without L-cysteine hydrochloride.

TABLE 1

Residual potency (%), amount of hardly soluble decomposition product produced (%) and turbidity after re-dissolution (hereinunder referred to R.P., D.P. and Tu, respectively)

| | | Additives | | | | |
|---|---|---|---|---|---|---|
| | | None | L-cysteine hydrochloride*1 (3 mg) | Citric acid (21 mg) sodium dihydrogenphosphate (35 mg)*1 | Maleic acid (1 mg)*1 | Glycine hydrochloride (14 mg)*1 |
| start | R.P. % | 100 | 100 | 100 | 100 | 100 |
| | D.P. % | 0 | 0 | 0 | 0 | 0 |
| | Tu*2 | None | None | None | None | None |
| 60° C. 3 days | R.P. % | 90 | 95 | 85 | 70 | 80 |
| | D.P. % | 0.2 | 0.1 | 1.5 | 0.2 | 0.1 |
| | Tu | None | None | X | None | None |
| 60° C. 7 days | R.P. % | 82 | 90 | 70 | 55 | 60 |
| | D.P. % | 0.5 | 0.1 | 3.1 | 0.4 | 0.2 |
| | Tu | X | None | X | X | None |

Notes
*1 amount of additives to compound A (20 mg potency)
*2 turbidity when re-dissolution was made with normal saline solution (10 ml) (modified from Mannual of Japanese Pharmacopoeia, 11th ed., 2nd method, i.e., a sample is dissolved in normal saline solution in place of distillated water for injection, and turbidity is observed with naked eye under about 1000 Lux right under a while light lamp)

Any amount and any method of addition may be employed, with respect to L-cysteine or salts thereof. Preferred amount of L-cysteine or salts thereof in the case of hydrochloride of the compound A is 0.1–50 mg, more preferably 0.6–9 mg every 20 mg potency of said hydrochloride, taking into account of stabilization degree or pharmacological activity of L-cysteine or salts thereof. pH should be 2–5, more preferably 2.5–3.5, taking into consideration of properties of the compound A. For instance, sodium hydroxide and hydrochloric acid may be added as a pH adjustment agent. Furthermore, a pharmaceutical composition of public, for example, fillers may be added, if desired.

Freeze-drying injection is prepared by dissolving the compound A or salts thereof with L-cysteine or salts

EXAMPLE 2

To hydrochloride of the compound A (20 mg potency) were added L-cysteine hydrochloride (12 mg) and lactose, a filler, (50 mg). The mixture was dissolved in distillated water for injection (10 ml) and then a small amount each of sodium hydroxide and hydrochloric acid was added thereto until pH was adjusted to about 2.5. The mixture was filtered under sterilization and filled in vials (18 ml each) which were then subjected to freeze-drying and sealed with rubber stoppers to obtain stabilized freeze-drying injection.

EXAMPLE 3

To hydrochloride of the compound A (20 mg potency) were added L-cysteine hydrochloride (3 mg) and lactose, a filler, (50 mg). The mixture was dissolved in distillated water for injection (10 ml) and then a small amount each of sodium hydroxide and hydrochloric acid was added thereto until pH was adjusted to about 3.0. The mixture was filtered under sterilization and filled in vials (18 ml each) which were then subjected to freeze-drying and sealed with rubber stoppers to obtain stabilized freeze-drying injection.

EXAMPLE 4

To hydrochloride of the compound A (20 mg potency) were added L-cysteine hydrochloride (0.5 mg) and maltose, a filler, (50 mg). The mixture was dissolved in distillated water for injection (10 ml) and then a small amount each of sodium hydroxide and hydrochloric acid was added thereto until pH was adjusted to about 3.5. The mixture was filtered under sterilization and filled in vials (18 ml each) which were then subjected to freeze-drying and sealed with rubber stoppers to obtain stabilized freeze-drying injection.

EXAMPLE 5

To hydrochloride of the compound A (10 mg potency) were added L-cysteine hydrochloride (2 mg) and sodium chloride, a filler, (90 mg). The mixture was dissolved in distillated water for injection (10 ml) and then a small amount each of sodium hydroxide and hydrochloric acid was added thereto until pH was adjusted to about 3.0. The mixture was filtered under sterilization and filled in vials (18 ml each) which were then subjected to freeze-drying and sealed with rubber stoppers to obtain stabilized freeze-drying injection.

EXAMPLE 6

To hydrochloride of the compound A (100 mg potency) were added L-cysteine hydrochloride (15 mg) and lactose, a filler, (250 mg). The mixture was dissolved in distillated water for injection (50 ml) and then a small amount each of sodium hydroxide and hydrochloric acid was added thereto until pH was adjusted to about 3.0. The mixture was filtered under sterilization and filled in vials (100 ml each) which were then subjected to freeze-drying and sealed with rubber stoppers to obtain stabilized freeze-drying injection.

TABLE 2

Residual potency (%), amount of hardly soluble decomposition product produced (%) and turbidity after re-dissolution (hereinunder referred to R.P., D.P. and Tu, respectively)

| | | Additives | | | | | |
|---|---|---|---|---|---|---|---|
| | | None | Example 2 | Example 3 | Example 4 | Example 5 | Example 6 |
| start | R.P. % | 100 | 100 | 100 | 100 | 100 | 100 |
| | D.P. % | 0 | 0 | 0 | 0 | 0 | 0 |
| | Tu*[1] | None | None | None | None | None | None |
| 60° C. | R.P. % | 82 | 90 | 92 | 92 | 93 | 90 |
| 7 days | D.P. % | 0.5 | 0.1 | 0.1 | 0.1 | 0.1 | 0.1 |
| | Tu*[1] | X | None | None | None | None | None |

Note
*[1]turbidity when re-dissolution was made with normal saline solution (10 ml)
(the same as in Note in TABLE 1)

What is claimed is:

1. A stable injectable composition consisting essentially of:
   (i) (7S, 9S)-9-acetyl-9-amino-7-[(2-deoxy-$\beta$-D-erythropentopyranosyl)oxy]-7,8,9,10-tetrahydro-6,11-dihydroxynaphthacene-5,12-dione or salts thereof; and
   (ii) L-cysteine or salts thereof, wherein the L-cysteine or the salts thereof are contained in an amount of 0.1 - 50 mg for every 20 mg potency of (7S, 9S)-9-acetyl-9-amino-7-[(2-deoxy-$\beta$-D-erythro-pentopyranosyl)oxy]-7,8,9,10-tetrahydro-6,11-dihydroxy-naphthacene-5,12-dione or salts thereof.

2. The composition according to claim 1, wherein said composition contains 0.6–9 mg of L-cysteine or salts thereof.

3. The composition according to claim 1, wherein the pH is 2–5.

4. The composition according to claim 3, wherein the pH is 2.5–3.5.

5. The composition according to claim 1, wherein the salts of (7S, 9S)-9-acetyl-9-amino-7-[(2-deoxy-$\beta$-D-erythropentopyranosyl)oxy]-7,8,9,10-tetrahydro-6,11-dihydroxynaphthacene-5,12-dione are hydrochloride, hydrobromide, citrate, tartrate, lactate, fumarate, maleate or methanesulfonate.

6. The composition according to claim 1, wherein the salts of L-cysteine are hydrochloride or sulfate.

7. A powdered composition consisting essentially of:
   (i) (7S, 9S)-9-acetyl-9-amino-7-[(2-deoxy-$\beta$-D-erythropentopyranosyl)oxy]-7,8,9,10-tetrahydro-6,11-dihydroxynaphthacene-5,12-dione or salts thereof; and
   (ii) L-cysteine or salts thereof,
   wherein the L-cysteine or the salts thereof are contained in an amount of 0.1–50 mg for every 20 mg potency of (7S, 9S)-9-acetyl-9-amino-7-[(2-deoxy-$\beta$-D-erythropentopyranosyl)oxy]-7,8,9,10-tetrahydro-6,11dihydroxynaphthacene-5,12-dione or salts thereof.

* * * * *